(12) United States Patent
Joyce et al.

(10) Patent No.: US 11,484,876 B2
(45) Date of Patent: Nov. 1, 2022

(54) SYSTEMS AND METHODS FOR AN E-GATING FEATURE IN AN ELECTROCHEMICAL TEST STRIP

(71) Applicant: POLYMER TECHNOLOGY SYSTEMS, INC., Whitestown, IN (US)

(72) Inventors: Joseph P. Joyce, Lafayette, IN (US); Matthew Musho, Wellsboro, PA (US)

(73) Assignee: POLYMER TECHNOLOGY SYSTEMS, INC., Whitestown, IN (US)

( * ) Notice: Subject to any disclaimer, the term of this patent is extended or adjusted under 35 U.S.C. 154(b) by 95 days.

(21) Appl. No.: 16/701,052

(22) Filed: Dec. 2, 2019

(65) Prior Publication Data

US 2020/0171483 A1 Jun. 4, 2020

Related U.S. Application Data

(60) Provisional application No. 62/774,290, filed on Dec. 2, 2018.

(51) Int. Cl.
*B01L 3/00* (2006.01)

(52) U.S. Cl.
CPC ........... *B01L 3/502* (2013.01); *B01L 2200/16* (2013.01); *B01L 2300/0825* (2013.01); *B01L 2300/0877* (2013.01); *B01L 2300/12* (2013.01); *B01L 2300/18* (2013.01); *B01L 2400/0627* (2013.01)

(58) Field of Classification Search
CPC ............ B01L 3/502; B01L 2300/0825; B01L 2200/16; B01L 2300/0877; B01L 2300/12; B01L 2400/0627; B01L 2300/18; B01L 3/502746; B01L 2300/0645; B01L 2300/165; B01L 2400/0688; B01L 2300/1827
See application file for complete search history.

(56) References Cited

U.S. PATENT DOCUMENTS

| | | | |
|---|---|---|---|
| 2003/0079987 A1 | 5/2003 | Hodges et al. | |
| 2006/0011539 A1* | 1/2006 | Lee | G01N 1/40 |
| | | | 210/613 |
| 2006/0194331 A1 | 8/2006 | Pamula et al. | |
| 2011/0302778 A1 | 12/2011 | Lee et al. | |
| 2012/0295269 A1 | 11/2012 | Pourahmad et al. | |
| 2013/0026051 A1 | 1/2013 | Nelson et al. | |
| 2013/0098777 A1 | 4/2013 | Gaustad | |
| 2013/0118899 A1* | 5/2013 | Chen | G01N 27/3272 |
| | | | 204/403.03 |

(Continued)

OTHER PUBLICATIONS

Chang et al. "Electrowetting on dielectric: a low voltage study on self-assembled monolayers and its wetting kinetics," 2004 International Conference on MEMS, NANO and Smart Systems (Aug. 25, 2004) (Year: 2004).*

(Continued)

*Primary Examiner* — Matthew D Krcha
*Assistant Examiner* — Sophia Y Lyle
(74) *Attorney, Agent, or Firm* — Haynes and Boone, LLP (57) ABSTRACT

A system for testing for an analyte includes a test strip. The test strip includes a first flow path. The test strip further includes a heating element in communication with a heating area of the first flow path, for heating a sample in the first flow path. The test strip further includes an e-gate, the e-gate in the first flow path, the e-gate separating the heating area from a detection area of the first flow path.

13 Claims, 4 Drawing Sheets

(56) References Cited

U.S. PATENT DOCUMENTS

2014/0194305 A1* 7/2014 Kayyem ........... B01L 3/502715
                                                        506/9
2016/0107951 A1   4/2016 Van Dam et al.
2016/0299138 A1* 10/2016 Almasri ................. B03C 5/005
2018/0251811 A1*  9/2018 Hughes ................. C12Q 1/004
2019/0321819 A1* 10/2019 Arango ............... B01L 3/50273

OTHER PUBLICATIONS

International Search Report and Written Opinion dated Feb. 18, 2020 issued in related PCT App. No. PCT/US2019/064062 (14 pages).

International Search Report and Written Opinion dated Feb. 18, 2020 issued in related PCT App. No. PCT/US2019/064060 (14 pages).

Srinivasan et al. "An integrated digital microfluidic lab-on-a-chip for clinical diagnostics on human physiological fluids," Lab on a Chip 4.4 (May 26, 2004): 310-315. Abstract, p. 311 col. 1, para 103; p. 312 col 1 para 3; p. 312 col 2 para 2; p. 313 col. 1 para 3; p. 313 col. 2 para 1-5; p. 314 col. 1 para 2-3; Figure 1; Figure 3; Figure 4; and Figure 5.

Chang et al. "Electrowetting on dielectric: a low voltage study on self-assembled monolayers and its wetting kinetics," 2004 International Conference on MEMS, NANO and Smart Systems (Aug. 25, 2004). Abstract; p. 1 col. 1 para 1-2; p. 1 col. 2 para 3; p. 2 col. 1 para 1; p. 6 col. 1 para 1; p. 6 col. 2 para 1.

Saeki et al. "Electrowetting on dielectrics (EWOD): reducing voltage requirements for microfluidics." Polym. Mater. Sci. Eng 85 (Aug. 2001): 12-13. p. 1 col. 1 para 104; p. 1 col. 1 para 9; p. 2 col. 1 para 1-2; Figure 1; and Figure 2.

Chung et al. "On-chip manipulation of objects using mobile oscillating bubbles," Journal of Micromechanics and Microengineering 18.12 (Nov. 19, 2008); 125024. Abstract, p. 2 col. 2 para 2; p. 3 col. 1 para 1; Figure 1; Figure 7.

\* cited by examiner

FIG. 4 ated test strip or EGTS). In many embodiments, an e-gated test strip includes a braking feature. By braking feature, it is meant to refer to a feature that stops of slows the flow of fluid in the test strip such that it does not completely advance into another area of the test strip. In many configurations, such braking features are implemented in a test strip utilizing microfluidics and/or capillary flow tubes. In many embodiments the braking feature is a hydrophobic glass bead dielectric that can be applied (screened) on top of the standard electric contacts on-strip. The thickness, wetting angle, feature geometry, potential applied, and channel height play important roles in the effectiveness of the design. In many embodiments, the braking feature is the ablated trough that is cut into the body of the base polymer film that the biosensor is fabricated from. The trough is a semicircular feature that has an approximate 1 to 1 ratio of diameter to fluid channel width. The depth and edge "sharpness" play a role in the reliability and longevity of the fluid to be held in place until the analyzer releases the fluid to the next stage. In many embodiments, the braking feature is a Self-Assembled Monolayer (SAM). This is a printed (screened or flood) process application that needs a temporary holding dam so that the fluid carrier can allow the features of the SAM to assemble properly and then remove the dam for the next component to be assembled. In many embodiments, the braking features do not need any external forces to function

SYSTEMS AND METHODS FOR AN E-GATING FEATURE IN AN ELECTROCHEMICAL TEST STRIP

CROSS REFERENCE TO RELATED APPLICATIONS

This application claims the benefit of U.S. provisional application No. 62/774,290, filed on Dec. 6, 2019, which is hereby incorporated by reference in its entirety.

BACKGROUND

In many scenarios, doctors, consumers, and health professionals desire to test for various analytes. Although lab testing is readily available for users, such testing requires users to send away samples and results will not usually be ready quickly. Therefore, point of care (POC) testing systems are desirable. Some of the biggest factors affecting the sale and use of POC testing systems is the convenience, disposability, and ease of use provided by various systems. Therefore, systems that provide such factors are highly desirable.

BRIEF SUMMARY

In one embodiment, a system for testing for an analyte includes a test strip. The test strip includes a first flow path and a time dependent area in the first flow path. The test strip includes an e-gate, the e-gate in the first flow path, the e-gate separating the time dependent area from a detection area of the first flow path. In one alternative, the time dependent area is a reaction holding area. In another alternative, the reaction holding area includes reagents for causing a reaction. Alternatively, the time dependent area is a heating area and includes a heating element in communication with the heating area of the first flow path, for heating a sample in the first flow path. In another alternative, the time dependent area is a temperature change area and includes a temperature change element in communication with the temperature change area of the first flow path, for changing the temperature a sample in the first flow path. Alternatively, the analyte is Hb A1C. In another alternative, the e-gate is a hydrophobic glass bead dielectric. Alternatively, the e-gate is an ablated trough that is cut into a body of a base of a polymer film that the test strip is made from. In another alternative, the e-gate a Self Assembled Monolayer (SAM). Alternatively, an electric current opens the e-gate. In another alternative, the detection area includes an interdigitated electrode for detecting A1C. Alternatively, the test strip further includes a second flow path, the second flow path including an interdigitated electrode for detecting hemoglobin. In another alternative, the system further includes a meter, the meter engaging the test strip, the meter configured to open the e-gate with an electric current. Alternatively, the meter is configured to open the e-gate when the sample has reached a necessary temperature. In another alternative, the meter is configured to open the e-gate when the sample has reached a necessary temperature. Alternatively, the meter is configured to open the e-gate after the sample has undergone necessary digestion. In another alternative, the meter is configured to open the e-gate after a preset period of time.

In one embodiment, a system for testing for an analyte includes a test strip. The test strip includes a first flow path and a time dependent area in the first flow path. The test strip includes an e-gate, the e-gate in the first flow path, the e-gate separating the time dependent area from a detection area of the first flow path. The e-gate is selected from a group consisting of a hydrophobic glass bead dielectric and a Self Assembled Monolayer (SAM).

In one embodiment, a method of holding a sample in a time dependent area of a test strip includes providing a test strip. The test strip includes a first flow path and a time dependent area in the first flow path. The test strip includes an e-gate, the e-gate in the first flow path, the e-gate separating the time dependent area from a detection area of the first flow path. The e-gate is selected from a group consisting of a hydrophobic glass bead dielectric and a Self Assembled Monolayer (SAM). The method includes applying a sample to the test strip. The method further includes flowing the sample along the first flow path. The method further includes holding the sample in the time dependent area with the e-gate. The method further includes electrically releasing the e-gate. The method further includes flowing the sample past the time dependent area. In one alternative, the time dependent area is a heating area and includes a heating element in communication with the heating area of the first

DETAILED DESCRIPTION

Certain terminology is used herein for convenience only and is not to be taken as a limitation on the embodiments of the system and methods for an e-gating feature in an electrochemical test strip (also referred to as an e-gated test and stop the flow of fluid. Instead they function automatically based on current applied via electrodes from a meter. In alternatives, other braking techniques may be used for the e-gate that may be actuated by a current and do not require mechanical pieces.

In many embodiments, the e-gated test strip is used in the detection of hemoglobin and hemoglobin A1C such that a ratio of the two is calculated. As part of this assay, in many configurations, the flow of the lysed sample is controlled in order to provide a proper sequence in the system. In many configurations, the e-gated test strip is constructed as a multi-layer film strip biosensor. In many configurations, the biosensor has highly engineered film layers that control biosensor detection, electrical signals, fluid flow and heat. Important to this application is the control of fluid flow and location.

In some embodiment the e-gated test strip integrates one of three differently fabricated, in-process braking features to provide a system that gives greatest reliability for control, near and long term. Of them, two of the three designs utilize an applied low voltage to the leading edge of the fluid to alter the wetting angle of the fluid so that the braking feature geometry is now misaligned and the capillary action of the wetted surfaces pulls or restarts the flow of the fluid into the measurement channel. The third braking feature takes advantage of the hydrophobic nature of a Self-Assembled Monolayer (SAM). The SAM has the ability to relax its hydrophobic characteristics due to an applied voltage and allow the fluid to restart into the measurement channel.

In many embodiments, the first braking feature is a hydrophobic glass bead dielectric that can be applied (screened) on top of the standard electric contacts on-strip. The thickness, wetting angle, feature geometry, potential applied, and channel height play important roles in the effectiveness of the design.

In many embodiments, the second braking feature design is the ablated trough that is cut into the body of the base polymer film that the biosensor is fabricated from. The trough is a semicircular feature that has an approximate 1 to 1 ratio of diameter to fluid channel width. The depth and edge "sharpness" play a role in the reliability and longevity of the fluid to be held in place until the analyzer releases the fluid to the next stage.

In many embodiments, the third braking feature is the Self-Assembled Monolayer (SAM). This is a printed (screened or flood) process application that needs a temporary holding dam so that the fluid carrier can allow the features of the SAM to assemble properly and then remove the dam for the next component to be assembled.

Numerous advantages exist for this, including:
1.) Increased consumer use reliability; less components lead to less process failure
2.) Lower inventory requirements and manufacturing time.
3.) Lower product cost
4.) Lower shipping packaging and transit costs.
5.) The E-gating allows for reduced physical component tolerance stack up.
6.) More accurate location control of the solution.

Figure 1:
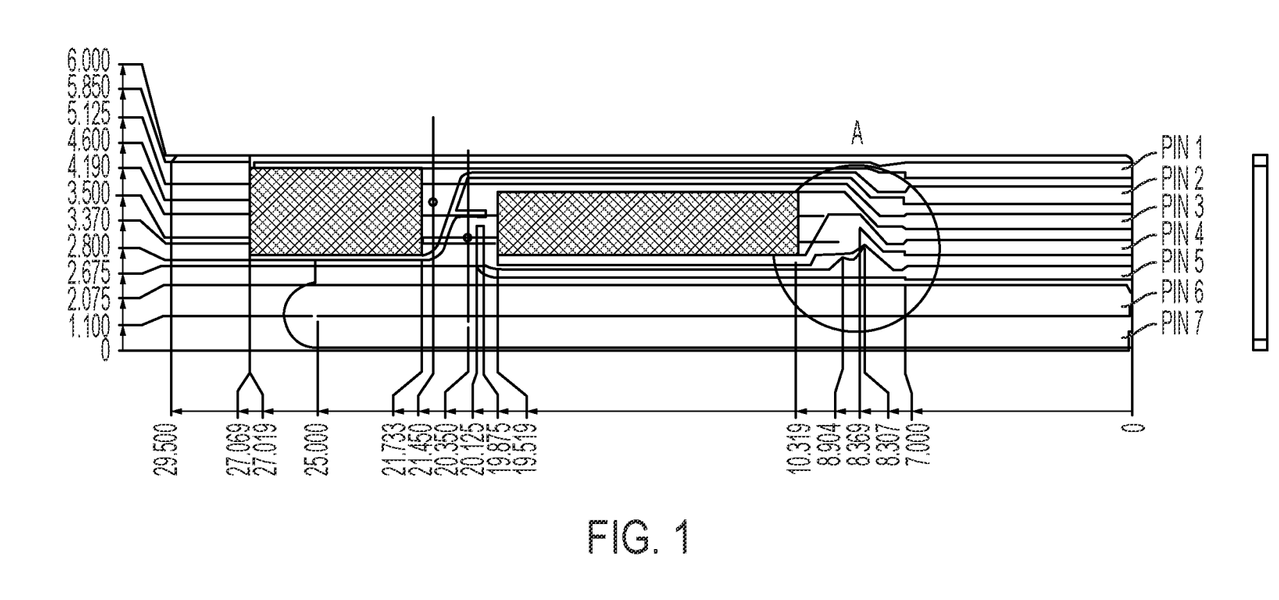
FIG. 1 shows a diagram of an embodiment of an e-gated electrochemical test strip.
Figure 2:
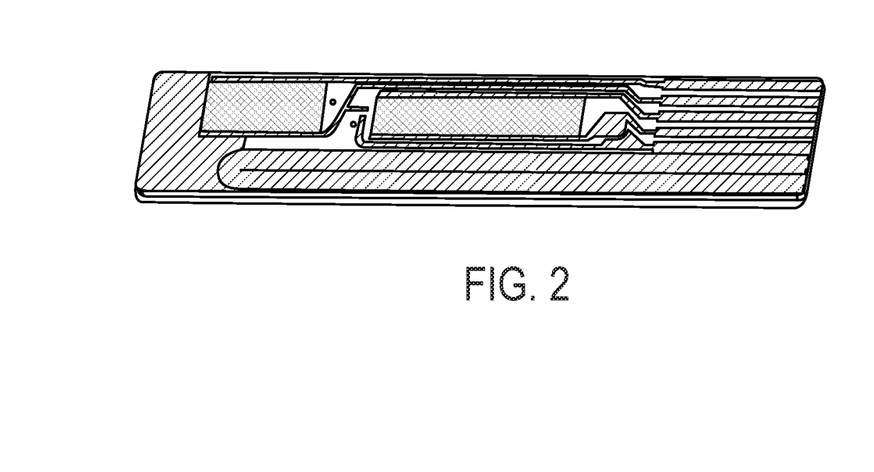
FIG. 2 shows a perspective view of a diagram of the e-gated electrochemical test strip of FIG. 1.
Figure 4:
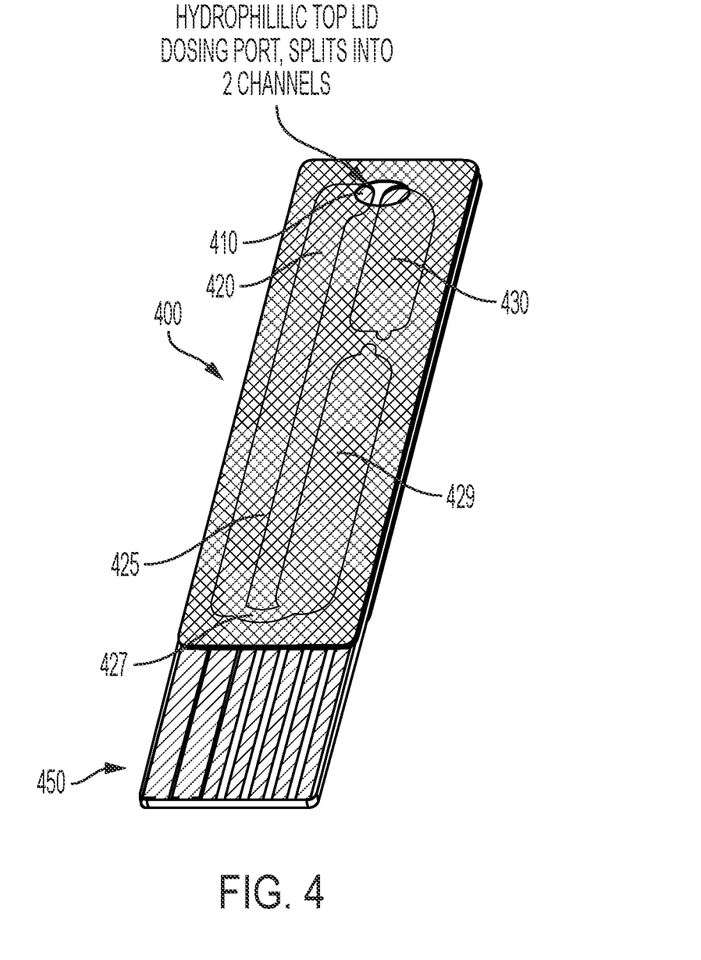
FIG. 4 shows another diagram of one embodiment of an e-gated test strip of FIG. 1.

FIG. 1 shows a diagram of an embodiment of an e-gated electrochemical test strip, with the indicated numbers showing distances on the x-y axis from the origin zero in the bottom right corner of the strip in cm for various components. These distances are purely exemplary. FIG. 4 shows a diagram of one embodiment of an e-gated test strip 400. In this diagram, the application port 410 is visible. Application port 410 is located in a hydrophobic cover for the strip. Also visible are the two flow channels of the device, A1C channel 420 and Hb channel 430. In A1C channel 420 there two primary areas, heating area 425 and detection area 429 which are separated by an e-gate 427. Also, the electrode leads 450 are visible. This setup is used because the Hb channel does not require heating/digestion, so the sample can proceed immediately to the detection area, whereas in the A1C channel 420, digestion is first necessary. The trace of the various circuitry is not visible in this configuration.

In many embodiments, in heating area 425, the sample is heated and digested. This may occur according to a variety of techniques; however, it is important to prevent the advance of the sample beyond. This is the purpose of the e-gate.

Table 1 below shows an explanation of the process flow for embodiments of a test strip including an e-gate. Typically, circuitry/logic in a meter controls the operation of the test strip, however, such control circuitry/logic may be resident in any device that engages the test strip. As shown in the table below and FIG. 4, the electrode and pin arrangement are shown. When the test strip is first introduced into the meter and the meter is activated, the system detects the strip via pin 6 and 7. This is event 1. These pins, 6 and 7, are part of a u-shaped trace. Pin 5 and pin 6 detect that heating area 425 has been filled. This is event 2. Pin 1 and pin 2 are provided for use in measuring the hemoglobin in the sample provided. This is event 3. Subsequently, in event 4, pin 6 and pin 7 cooperate to heat the sample for the A1C side of the test in event 4. Once the sample is sufficiently heated, the pins 4, 5, and 6 are used to release the e-gate, in event 5. In event 6, Pin 2 and 5 are used to detect a fill of the A1C detection area 429. Subsequently, in event 7, pin 3 and pin 4 provide for the detection and measurement of A1C, providing a counter electrode and a working electrode.

| PIN # | CHEMISTRY | Signal | | | | | | |
|---|---|---|---|---|---|---|---|---|
| | | Event 1 | Event 2 | Event 3 | Event 4 | Event 5 | Event 6 | Event 7 |
| 1 | Hb | | | Counter | | | | |
| 2 | Hb | | | Working | | | Fill A1C | |
| 3 | A1C | | | | | | | Counter |
| 4 | A1C | | | | | Release E-Gate | | Working |
| 5 | A1C | | Heat Channel Fill | | | Release E-Gate | Fill A1C | |

-continued

| PIN | | Signal | | | | | | |
|---|---|---|---|---|---|---|---|---|
| # | CHEMISTRY | Event 1 | Event 2 | Event 3 | Event 4 | Event 5 | Event 6 | Event 7 |
| 6 | A1C | Strip Detect | Heat Channel Fill | | Heat | Release E-Gate | | |
| 7 | | Strip Detect | | | Heat | | | |

Figure 3A:
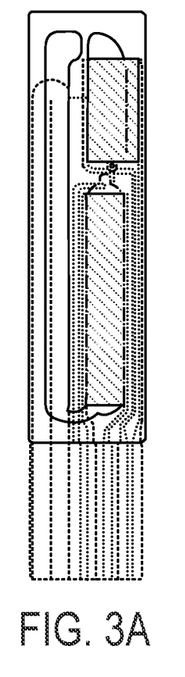
FIG. 3A-3C show additional diagrams of the e-gated electrochemical test strip of FIG. 1.
Figure 3B:
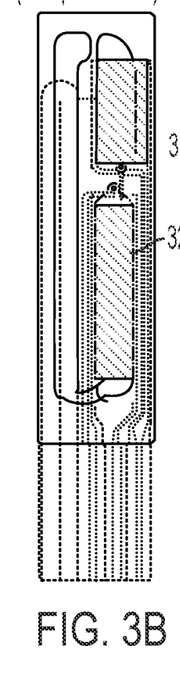
Figure 3C:
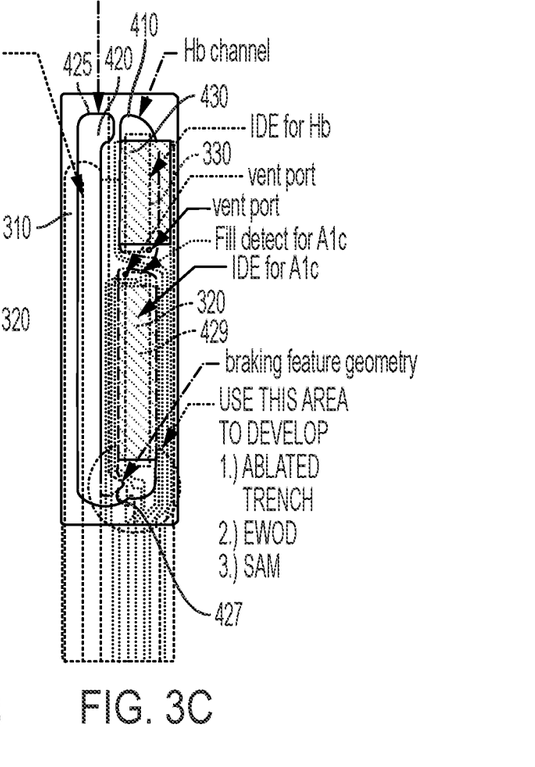

FIG. 3A-3C provide more detail concerning the system. As shown in 3C, a heating/digestion channel or heating area 425, 425 on the A1C channel 420 side is provided. Under this channel is the gold resistive heating element 310 that also provides for the detection of the insertion of the strip. One of three possible techniques for e-gating is used at e-gate 427. Subsequently, in detection area 429 an interdigitated electrode 320 for A1C is located that allows for the measurement of A1C. On the Hb channel 430, a Hb interdigitated electrode 330 is provided for the measurement of hemoglobin.

Therefore, in many embodiments, a test strip is provided that has a single stage electrochemical detection system and a dual stage electrochemical detection system. A single port leads to both electrochemical detection systems and the flow paths for each. On the single stage electrochemical detection system side, the flow path leads to a working electrode and counter electrode arrangement, whereby a level of a first analyte may be detected. One the dual stage electrochemical detection system side, the flow path first leads to a heating/digestion area. This area is separated from a detection area via an e-gate. The e-gate may automatically be opened and triggered by the meter (or other electrical source) connected to the test strip. Once the sample is heated/digested sufficiently, the gate is opened and the sample proceeds to the detection area. In many embodiments the single stage electrochemical detection system is for Hb. In many embodiments, the dual stage electrochemical detection system is for A1C.

In many embodiments, a meter associated with the e-gated test strip includes logic for running the test, including, but not limited to, logic for detecting when/whether the strip is inserted; logic for beginning the testing; logic for determining when the heating area is filled; logic for activating the heating element in the heating area; logic for releasing the e-gate when the sample is sufficiently digested/heated; logic for determining when the A1C testing area is full; logic for activating the electrodes for determining A1C levels; logic for determining when the Hb testing area is full; logic for activating the electrodes for determining A1C levels; logic for outputting a result (in many scenarios including the ratio of Hb/A1C). In many scenarios, this logic includes activating and deactivating various electrodes/leads by providing current or voltage to the pins as discussed above.

In many alternatives, the heating area may be a time dependent area, where the sample is held by the e-gate to accomplish a goal of an assay. In some embodiments, this may be a waiting area for a reaction to occur. In other embodiments, this is a holding area where a reactant is added. In other embodiments, this is a heating area, where a sample may be heated. Alternatively, a sample may be cooled in this area. Alternatively, the e-gate may hold the sample in the time dependent area until another metric is reached, such as a temperature, a measured voltage, a measured current, a measured pH, a measured color change, a measured time, a measured fluorescence. Sensors may be located in the time dependent area in order to accomplish this detection step.

In many embodiments, it may be necessary to build and test electrowetting values. As such, described herein are some possible protocols for doing so. Electro-wetting (hydrophobic) valves are involved in the stopping and starting of fluid flow in a capillary channel. Flow stoppage occurs when the sum of contact angles for top and bottom surface exceed a critical value. In a typical capillary channel one surface is very hydrophilic and the other can be anywhere from hydrophilic to slightly hydrophobic. If the top surface becomes less hydrophilic, then it is possible to stop fluid flow by providing a hydrophobic area or patch on the bottom surface. There are at least two possible methods for constructing a hydrophobic region in a capillary: (1) coating a hydrophobic layer or (2) creating a self-assembling monolayer (SAM) across the channel width on one surface.

Restarting the fluid requires the hydrophobic character to relax or dissipate. In both approaches a low voltage is used to cause the loss of hydrophobicity. In the first approach a dielectric coating is used which accumulates a charge and therefore increase its surface energy (i.e. lowers the contact angle). In the second approach the SAM's hydrophilic head group (which is attaches the SAM to the electrode surface) is repelled from the surface. Once the fluid begins to flow, the valve will not stop the fluid flow. In the first approach, known electro-wetting on dielectric (EWOD), an electrode is positioned under the valve and a dielectric layer is covers the electrode. In the second approach, an electrode is positioned in the valve region and a SAM is created directly on the electrode.

In order to fabricate and test a non-continuous fluid flow in a capillary channel using hydrophobic valves, it may be necessary to configure the electro-wetting system. In one embodiment, the testing involves providing test fluids in the form of whole blood and SMBG control solutions.

In order test a EWOD device, one is first created. In one embodiment, this process involves creating an EWOD using Sputtered Au (50 nm) on 0.25 mm white PET, Spacer tape (100 to 150 micron) double-sided tape, UV-cured dielectric ink: Dupont glass-filled ink and unfilled ink, Lid material: AR hydrophilic lid and 100-125 micron clear PET.

In order test a SAM device, one is first created. In one embodiment, this process involves creating an SAM using Sputtered Au (50 nm) on 0.25 mm white PET ($O_2$ plasma cleaned), Spacer tape (100 to 150 micron) double-sided tape, SAM: 1-hexanethiol; 95% ACS ethanol, distilled water, Lid material: AR hydrophilic lid and 100-125 micron clear PET Spacer tape, and Protective lamination with cutouts over the valve region. In order to perform one embodiment of the testing, a Shallow basin for SAM reaction (3-4), a Voltage Source, a (Video) Camera (optional), and a Hot plate.

In order to fabricate embodiments of a EWOD device, first one creates an electrode pattern in Au film using laser ablation at CTI. Then one prints dielectric pattern over Au electrodes using dielectric ink. One subset using glass-filled UV-cured dielectric and another subset with the same dielectric ink but without glass filler is created. Each subset that was created is assembled with a spacer layer. Each subset that was created is assembled with either AR hydrophilic lid or clear PET.

In order to create the SAM device, first an electrode pattern was created in Au film using laser ablation. Then a subset of ablated parts was cleaned using an oxygen plasma. Then a SAM layer was created for each part. 0.1M ethanolic water was mixed by dissolving 4.6 g of ethanol in 1 liter of distilled water in a clean beaker (for a volumetric flask, then add enough water to 4.6 g of ethanol to make a liter). Then the mixture was mixed with a clean stirrer for a minute.

To create 1 mM 1-hexanethiol solution, the following steps were taken. In a hood 0.12 g 1-hexanethiol was weighed out in a beaker or volumetric flask for every liter of desired SAM solution. One liter of 0.1M ethanolic water was added. This was mixed with a clean stirrer for a couple of minutes and then sealed tightly for use under a hood.

In order to create a SAM at room temperature, first in the hood pour 1 mM 1-hexanediol into a shallow basin. Then laminate protect lamination onto the ablated gold surface so that the valve regions are exposed but the reference electrodes are covered. Then place test parts that were plasma treated from (a) with their electrode parts facing down into SAM fluid for 10 minutes. Cover the basin to minimize evaporation and odors. Then remove the test parts from the SAM solution and wash with ethanol by dipping the parts in a succession (2-3) of shallow basins containing ethanol. Allow the parts to dry in the hood. If it is need, then dry by blowing nitrogen across the parts. Then remove protective lamination and store the parts in a sealed container until they are ready for assembly. Also, assemble then created subset and the subset that was not plasma treated or coated with a SAM from with a spacer layer. Then assemble each subset in with either AR hydrophilic lid or clear PET.

Then below table provides for a listing of the subsets created for testing.

| Prototype Number | Type | Electrode Covering | Lid |
|---|---|---|---|
| 1 | EWOD | Glass-filled dielectric | AR Hydrophilic |
| 2 | EWOD | Glass-filled dielectric | Untreated PET |
| 3 | EWOD | Dielectric | AR Hydrophilic |
| 4 | EWOD | Dielectric | Untreated PET |
| 5 | SAM | 1-hexanethiol | AR Hydrophilic |
| 6 | SAM | 1-hexanethiol | Untreated PET |
| 7 | SAM | Untreated | AR Hydrophilic |
| 8 | SAM | Untreated | Untreated PET |

Figure 5:
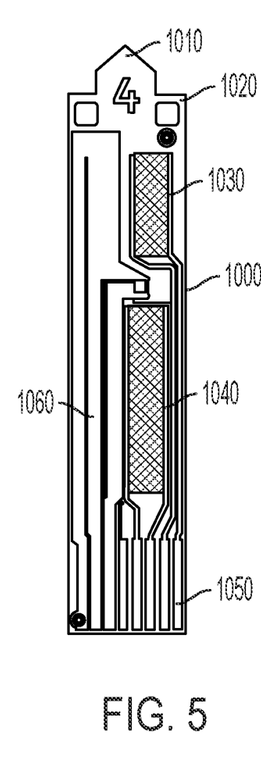
FIG. 5 shows another embodiment of a test strip for an ICA (Integrated Consumable Assay)

FIG. 5 shows another embodiment of a test strip for an ICA, specifically the substrate piece. This test strip 1000 is specifically designed to include a piercing end 1010. The strip also includes a stop 1020 to prevent the strip from advancing too far. In this embodiment, the piercing end 1010 is designed to pierce a reservoir that holds reactants or lysing agents (or some other material for interacting with the sample). Additionally, in this view, electrode areas 1030, 1040 are shown. In many embodiments these are interdigitated electrodes but other configurations are possible. Leads 1050 interact with a meter in order to power the strip to detect the analyte of interest. In alternatives, the strip may still include the piercing end 1010, however may be an optical strip. Electrodes 1060 provides for a heating element, that may heat a sample by powering the electrodes. Additionally, at finger 1140 shown in FIG. 6, the two leads located at 1070 provide electrical energy to electrically active the e-gate located at this area.

Figure 6:
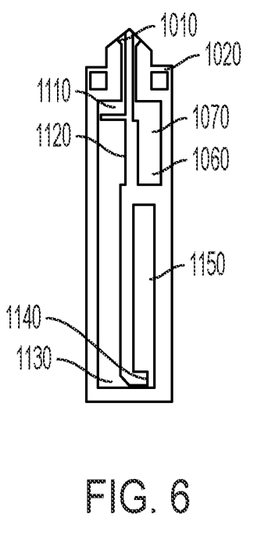
FIG. 6 shows the flow areas for the test strip of FIG. 5.

FIG. 6 shows the flow path etching that is laid over the substrate piece of FIG. 6. Additionally, a cover, not show, is laid over the substrate. Similarly, the device includes pierce point 1010 that aligns with the pierce point 1010 on the substrate. The strip also includes a stop 1020 to prevent the strip from advancing too far. Typically the channels of the device rely on capillary type flow action and include vents 1130, 1160 in the cover that is laid over the spacer. The device includes a digestion finger 1110 and digestion channel 1120, where the sample may be heated such that digestion can occur. In alternative embodiments, other chemical procedures may occur in this channel. A1C finger 1140 leads to electrode area 1040 where electrochemical testing may occur. The A1C channel 1150 lead to the area over electrode area 1040. Additionally, including is a channel that does not require digestion, channel 1170 over electrode 1030. This channel 1170 includes a vent 1160 in the cover. In many embodiments this channel is a hemoglobin channel.

In order to test the SAM on various Au valves, there are 3 different valve sizes that are 0.05, 0.10 and 0.20 mm wide in the capillary flow direction. Several reference electrodes are provided to test the influence of their position on the valve performance. These valves can be used once the valve is opened. The testing protocol is as follows:

1. Attach voltage source with the negative side connected to the gate (lead 2) and the positive side to the reference electrode (lead 1).
2. Inoculate the capillary channel with enough fluid (control solution) to fill just past the first valve (located at the bottom of the digestion chamber).
   a. If the fluid does not stop, then continue to add fluid until it stops at either valve 2 or 3 or it reaches the vent hole in the A1c chamber.
   b. If the fluid does stop, then turn on the voltage source to 0.5V.
      i. If the fluid does not start moving within 10 seconds, then increase the voltage in 0.5V increments until the fluid moves and the voltage does not exceed 5v.
         1. If the liquid does not start to move, then switch the positive lead from lead 1 to lead 3. Repeat the voltage application as in (1).
         2. If the liquid still does not move, then try to push the fluid past the valve to the second valve by applying some pressure to the fluid.
      ii. Add more fluid to the inoculation port.
         1. If the fluid stops again at either valve 2 or 3, then repeat applying the voltage as in (i). The other connection options are leads 4 and 3 for valve 2 and 5 and 3 for valve 3.
   b. Repeat the above protocol with lysed whole blood.

There are 4 EWOD valves that are 0.05, 0.10, 0.15 and 0.20 mm wide in the capillary flow direction. Reference electrodes for each valve are located upstream from their respective valve. These valves are re-usable. However, once the fluid is past the valve, the fluid flow cannot be stopped even if the voltage is removed. The testing protocol is as follows:

1. Attach voltage source with the negative side connected to the gate (lead 1) and the positive side to the reference electrode (lead 3).

2. Inoculate the capillary channel with enough fluid (control solution) to fill just past the first valve (located at the bottom of the digestion chamber).
   a. If the fluid does not stop, then continue to add fluid until it stops at either one of the other valves or it reaches the vent hole in the A1c chamber.
   b. If the fluid does stop, then turn on the voltage source to 0.5V.
      i. If the fluid does not start moving within 10 seconds, then increase the voltage in 0.5V increments until the fluid moves and the voltage does not exceed 5v.
         1. If the liquid still does not move, then try to push the fluid past the valve to the second valve by applying some pressure to the fluid.
      ii. Add more fluid to the inoculation port.
         1. If the fluid stops again at any of the other 3 valves, then repeat applying the voltage as in (i). The other connection options are leads 2 and 3 for valve 2, 4 and 3 for valve 3 and 5 and 3 for valve 4.
3. Repeat the above protocol with lysed whole blood.

In many embodiments, parts of the system are provided in devices including microprocessors. Various embodiments of the systems and methods described herein may be implemented fully or partially in software and/or firmware. This software and/or firmware may take the form of instructions contained in or on a non-transitory computer-readable storage medium. Those instructions then may be read and executed by one or more processors to enable performance of the operations described herein. The instructions may be in any suitable form such as, but not limited to, source code, compiled code, interpreted code, executable code, static code, dynamic code, and the like. Such a computer-readable medium may include any tangible non-transitory medium for storing information in a form readable by one or more computers such as, but not limited to, read only memory (ROM); random access memory (RAM); magnetic disk storage media; optical storage media; a flash memory, etc.

Embodiments of the systems and methods described herein may be implemented in a variety of systems including, but not limited to, smartphones, tablets, laptops, and combinations of computing devices and cloud computing resources. For instance, portions of the operations may occur in one device, and other operations may occur at a remote location, such as a remote server or servers. For instance, the collection of the data may occur at a smartphone, and the data analysis may occur at a server or in a cloud computing resource. Any single computing device or combination of computing devices may execute the methods described.

In sum, with respect to the description herein, numerous specific details are provided, such as examples of components and/or methods, to provide a thorough teaching and understanding of embodiments of the present invention. One skilled in the relevant art will recognize, however, that an embodiment can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Similarly, embodiments can be implemented in many forms, and based on the disclosure and teachings provided herein, a person of ordinary skill in the art will appreciate other ways and/or methods to implement an equivalent. Reference throughout this specification to "one embodiment", "an embodiment", or "a specific embodiment" means that a particular feature, structure, or characteristic described in connection with the embodiment is included in at least one embodiment and not necessarily in all embodiments. Thus, respective appearances of the phrases "in one embodiment", "in an embodiment", or "in a specific embodiment" in various places throughout this specification are not necessarily referring to the same embodiment.

Furthermore, the particular features, structures, or characteristics of any specific embodiment may be combined in any suitable manner with one or more other embodiments. It is to be understood that other variations and modifications of the embodiments described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as otherwise operable in certain cases, as is useful in accordance with a particular application.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The foregoing description of illustrated embodiments, including what is described in the Abstract and the Summary and the overview paragraphs, are not intended to be exhaustive or to limit the disclosed system, apparatuses, methods, compositions of matter or other disclosed subject matter to the precise forms disclosed herein. While specific embodiments of, and examples for, the disclosed system, apparatuses, methods, compositions of matter or other disclosed subject matter are described herein for teaching-by-illustration purposes only, various equivalent modifications are possible within the spirit and scope of the disclosed system, apparatuses, methods, compositions of matter or other disclosed subject matter, as those skilled in the relevant art will recognize and appreciate. As indicated, these modifications may be made in light of the foregoing description of illustrated embodiments and are to be included within the true spirit and scope of the disclosure herein provided.

What is claimed as new and desired to be protected by Letters Patent of the United States is:

1. A system for testing for an analyte, the system comprising:
   a test strip including:
      a first flow path;
      a time dependent area in the first flow path;
      an e-gate, the e-gate in the first flow path, the e-gate separating the time dependent area from a detection area of the first flow path, wherein the e-gate is a hydrophobic glass bead dielectric.

2. The system of claim 1, wherein the time dependent area is a reaction holding area.

3. The system of claim 2, wherein the reaction holding area includes reagents for causing a reaction.

4. The system of claim 1, wherein the time dependent area is a heating area and includes a heating element in communication with the heating area of the first flow path, for heating a sample in the first flow path.

5. The system of claim 1, wherein the time dependent area is a temperature change area and includes a temperature change element in communication with the temperature change area of the first flow path, for changing the temperature of a sample in the first flow path.

6. The system of claim 1, wherein the analyte is Hb A1C.

7. The system of claim 1, wherein an electric current opens the e-gate.

8. The system of claim 1, wherein the detection area includes an interdigitated electrode for detecting A1C.

9. The system of claim 8, wherein the test strip further includes a second flow path, the second flow path including an interdigitated electrode for detecting hemoglobin.

10. The system of claim 1, further comprising a meter, the meter engaging the test strip, the meter configured to open the e-gate with an electric current.

11. The system of claim 10, wherein the meter is configured to open the e-gate when the sample has reached a necessary temperature.

12. The system of claim 10, wherein the meter is configured to open the e-gate after the sample has undergone necessary digestion.

13. The system of claim 10, wherein the meter is configured to open the e-gate after a preset period of time.

\* \* \* \* \*